United States Patent
Hsu et al.

(10) Patent No.: US 8,321,133 B2
(45) Date of Patent: Nov. 27, 2012

(54) MEASUREMENT OF SOUND SPEED OF DOWNHOLE FLUID UTILIZING TUBE WAVES

(75) Inventors: Chaur-Jian Hsu, Danbury, CT (US); Ralph M. D'Angelo, New Fairfield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/877,047

(22) Filed: Oct. 23, 2007

(65) Prior Publication Data

US 2009/0105957 A1    Apr. 23, 2009

(51) Int. Cl.
*G01N 15/08* (2006.01)
(52) U.S. Cl. ............. 702/12; 702/39; 702/45; 702/50
(58) Field of Classification Search .......... 702/12, 702/39, 45, 50; 73/24.01, 54.41, 152.24; 175/40, 50
See application file for complete search history.

(56) References Cited

U.S. PATENT DOCUMENTS

| | | | |
|---|---|---|---|
| 4,628,725 A | | 12/1986 | Gouilloud et al. |
| 5,331,604 A | * | 7/1994 | Chang et al. ............ 367/31 |
| 5,485,431 A | * | 1/1996 | Johnson et al. .......... 367/30 |
| 5,831,934 A | * | 11/1998 | Gill et al. ................ 367/25 |
| 5,995,449 A | * | 11/1999 | Green et al. ............. 367/83 |
| 6,205,087 B1 | | 3/2001 | Fukuhara et al. |
| 6,817,229 B2 | * | 11/2004 | Han et al. ................ 73/64.53 |
| 6,938,470 B2 | * | 9/2005 | DiFoggio et al. ........ 175/50 |
| 6,957,572 B1 | | 10/2005 | Wu |
| 7,095,676 B2 | | 8/2006 | D'Angelo et al. |
| 2005/0034530 A1 | | 2/2005 | Han et al. |
| 2006/0120217 A1 | | 6/2006 | Wu et al. |

FOREIGN PATENT DOCUMENTS

| | | |
|---|---|---|
| EP | 1441105 A1 | 7/2004 |
| JP | 9211142 A | 8/1997 |
| WO | 2009029860 A1 | 3/2009 |

OTHER PUBLICATIONS

Brie, A., et al., Quantitative Formation Permeability Evaluation from Stoneley Waves, SPE Reservoir Eval. & Eng., Apr. 2000, pp. 109-117, vol. 3, No. 2.
Hsu, C.J., et al., Tube waves and mandrel modes: Experiment and theory, J. Acoust. Soc. Am, Dec. 1997, pp. 3277-3289, vol. 102, No. 6.
Kimball, C.V., et al., Semblance processing of borehole acoustic array data, Geophysics, Mar. 1984, pp. 274-281, vol. 49, No. 3.

(Continued)

*Primary Examiner* — Mohamed Charioui
*Assistant Examiner* — Elias Desta

(57) ABSTRACT

A technique for utilizing tube waves to measure sound speed of fluids and other properties in the frequency range of about 5 to 100 kHz. A drill string is equipped with a sensor tube having a cavity filled with a downhole fluid such as borehole mud or formation fluid. An acoustic transmitter and an array of acoustic receivers are mounted on the tube in direct contact with the fluid. Processing circuitry calculates a property, e.g., sound speed, of the fluid based on time-of-flight of an acoustic signal generated by the transmitter and received by the array of receivers. Alternatively change in signal phase as a function of frequency may be employed by the processing circuitry. The technique is particularly suited to measuring the sound speed of borehole mud in situ.

35 Claims, 6 Drawing Sheets

OTHER PUBLICATIONS

Lang, S.W., et al., Estimating slowness dispersion from arrays of sonic logging waveforms, Geophysics, Apr. 1987, pp. 530-544, vol. 52, No. 4.

Selfridge, A.R., Approximate Material Properties in Isotropic Materials, IEEE Transactions on Sonics and Ultrasonics, May 1985, pp. 381-394, vol. SU-32, No. 3.

Lide, D.R., Attenuation and Speed of Sound in Air As a Function of Humidity and Frequency, CRC Handbook of Chemistry and Physics 81st Edition, 2000-2001, CRC Press LLC, p. 14-40.

White, J.E., Underground Sound, Methods in Geochemistry and Geophysics, 18, 1983, Elsevier Science Publishers, pp. 146-147.

Kinsler, et al., Fundamentals of Acoustics, 3rd edition, Chapter 10, Wiley & Sons, 1982, pp. 225-228.

Hsu, Measurement of Sound Speed of Downhole Fluid by Helmholtz Resonator, U.S. Appl. No. 11/877,114, Oct. 23, 2007.

Examination Report of British Application Serial No. GB0918187.6 dated Sep. 20, 2001.

* cited by examiner

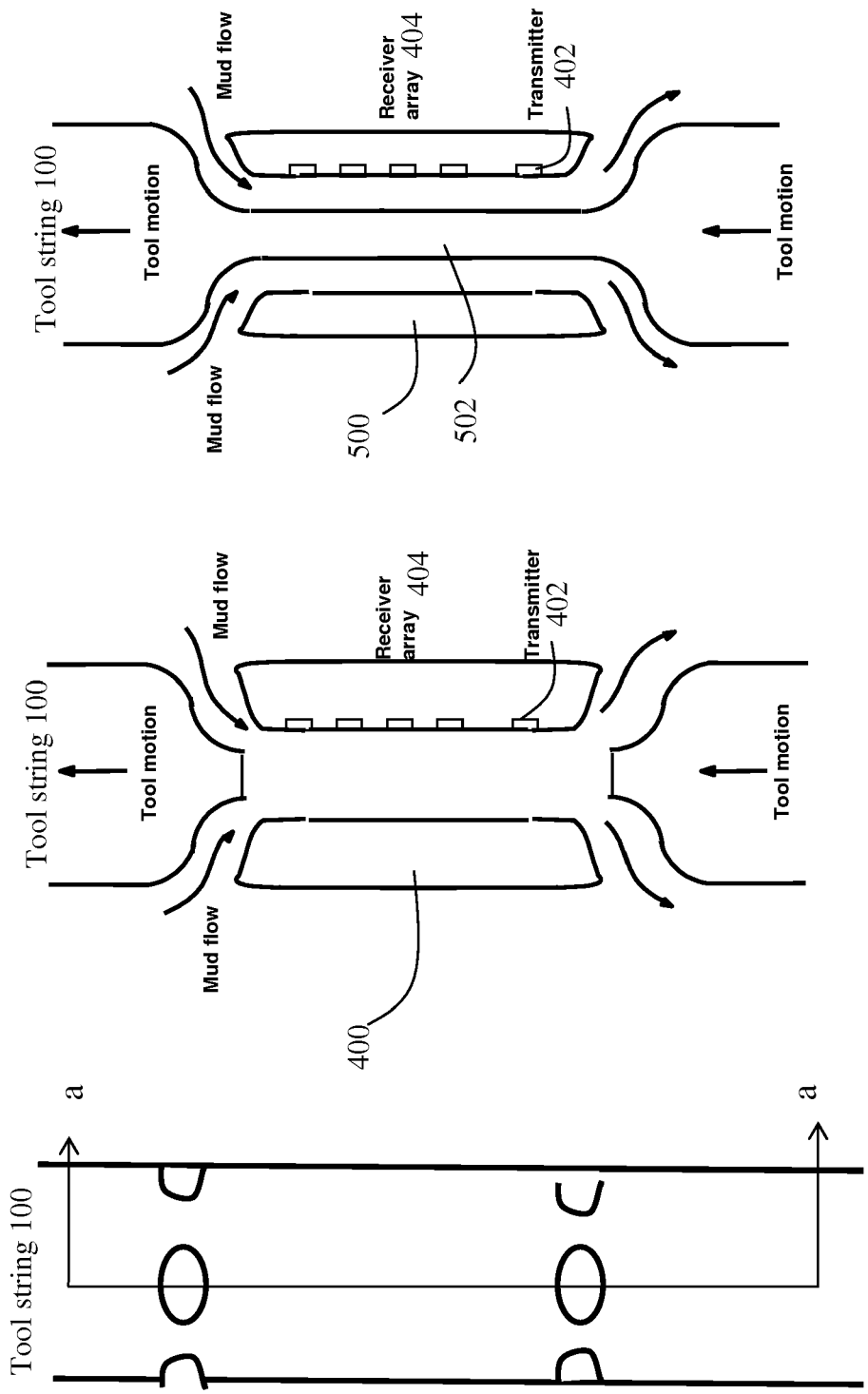
Figure 6 — Cross section a-a of another embodiment
Figure 5 — Cross section a-a of one embodiment
Figure 4 — Side view

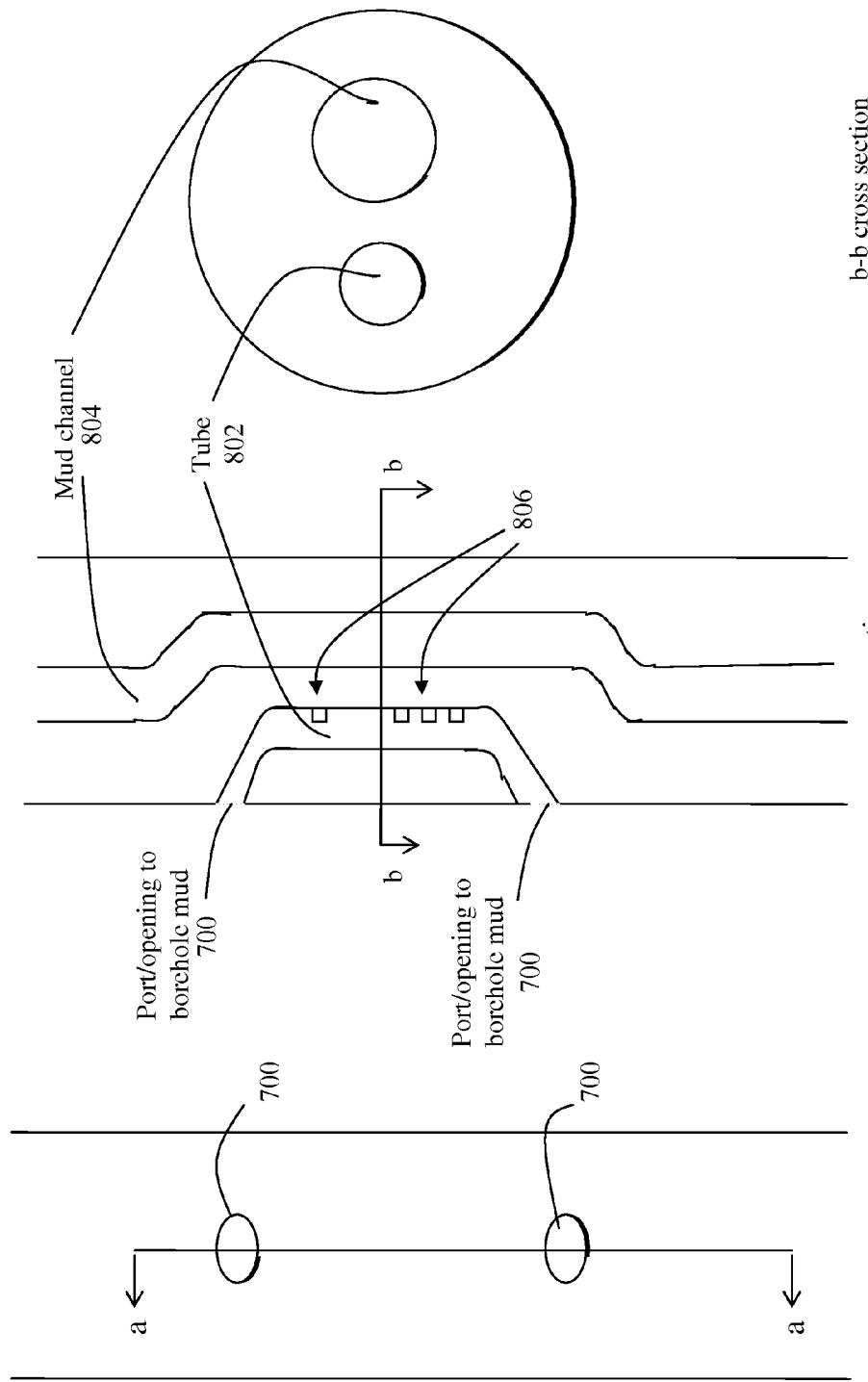

MEASUREMENT OF SOUND SPEED OF DOWNHOLE FLUID UTILIZING TUBE WAVES

BACKGROUND OF THE INVENTION

1. Field of the Invention

This invention is generally related to analysis of subterranean formations, and more particularly to measurement of the speed of sound in a downhole fluid in order to facilitate acoustic logging operations for formation evaluation and reservoir characterization.

2. Background of the Invention

Wireline and logging-while-drilling (LWD) tools are used to measure physical, chemical, and structural characteristics of formations surrounding a borehole. For example, data gathered by logging tools can be used to interpret formation stratigraphy, lithology, mineralogy, and pore fluid content. Logging tools typically emit one or more of an acoustic, electromagnetic and optical signal, and measure the response to that signal. In the case of acoustic logging tools, changes in amplitude, phase and speed can be utilized to characterize the formation. Some acoustic logging tools utilize modal propagations, such as Stoneley, dipole and quadrupole modes, to measure formation compressional and shear speeds. Examples include measurement of formation shear speed from borehole flexural (a.k.a. dipole) modes in wireline logging, extraction of formation shear speed from borehole quadrupole mode in logging while drilling, and to a lesser extent extraction of formation compressional speed from "leaky" fluid modes. These acoustic logging tools operate based on the dependence of the speed of the borehole modes on formation acoustic properties. However, the speed of the modes is also dependent on the acoustic speed of downhole fluids such as borehole mud. It is therefore desirable to measure independently the sound speed of downhole fluids in order to more accurately characterize the formation. Characterization of downhole formation fluid is of great interest, since it is often the motivation of the entire drilling activity.

A wide variety of equipment is available to measure sound speed of fluids outside the borehole environment. However, measuring the sound speed of downhole fluids outside the borehole can be problematic because the sound speed of a fluid is a function of its constituents, temperature and pressure. Since temperature and pressure tend to change when a borehole fluid is transported to the surface, and in addition, the fluid constituents, temperature and pressure at a given location in the borehole may also change over the time of drilling and production of the well, it would therefore be desirable to have a better technique to measure the sound speed of downhole fluids.

SUMMARY OF THE INVENTION

The present invention relates to an apparatus for facilitating analysis of a subterranean formation. The apparatus can comprise of a tube having the inside filled with a downhole fluid. The apparatus further can include at least one acoustic transmitter operable to generate at least one acoustic signal which is propagated through the downhole fluid in the tube cavity. Further, the apparatus can include at least one acoustic receiver operable to receive the acoustic signal. The apparatus also includes circuitry operative to compare a characteristic of the at least one received acoustic signal with at least one other signal so as to calculate a property of the fluid based on the comparison. The at least one other signal can be either at least one other received acoustic signal, the generated acoustic signal, or both. The property of the fluid may be stored in a memory, sent to the surface via telemetry, or both.

In accordance with another embodiment of the invention, a method for facilitating analysis of a subterranean formation. The method can comprise of causing a tube having a cavity to become filled with a downhole fluid, and then generating, with at least one acoustic transmitter, at least one acoustic signal which is propagated through the downhole fluid in the tube cavity. Then, the method further includes receiving, with at least one acoustic receiver, the acoustic signal, and comparing a characteristic of the at least one received acoustic signal with at least one other signal, and calculating a property of the fluid based on the comparison. Finally, the method can include at least one other signal that may be the generated acoustic signal, at least one other received acoustic signal, or both. The property of the fluid may be stored in a memory, sent to the surface via telemetry, or both.

One advantage of using tube waves to measure sound speed of downhole fluids is that typical tube geometry is simple and relatively easy to be adapted to wireline and LWD tool geometry. Also, the tube can be made part of a flow line, which helps to keep the test volume filled with local fluid, i.e., such that its constituents have not been contaminated, in comparison with a sample that is transported to the surface. Measurement accuracy is enhanced because, at the time of measurement, the fluid is subject to ambient conditions of the location, e.g., temperature, pressure, and gas influx.

Another advantage is that tube waves, being the lowest order mode in a fluid-filled tube, i.e., being the dominant mode at low frequencies, are relatively easy to excite and detect.

Another advantage of using tube waves is that the tube wave speed is measured over a length scale of wavelength, which is significantly, up to one order of magnitude, greater than the ID of the tube. This relatively large test volume will reflect heterogeneities such as small solid particles, cuttings, or gas bubbles in the volume averaged speed instead of large fluctuations in time.

The present invention is directed to an apparatus for facilitating analysis of subterranean formations. The apparatus includes a tube filled with a fluid, and at least one acoustic transmitter operable to generate at least one acoustic signal which is propagated through the fluid in a cavity of the tube. The apparatus further includes at least one acoustic receiver operable to receive the at least one acoustic signal. Finally, the apparatus includes circuitry operative to compare a characteristic of a first received acoustic signal of the at least one acoustic signal and a second signal, so as to calculate a property of the fluid based on the comparison.

According to one aspect of the invention, the apparatus may include the second signal which can be selected from the group consisting of at least one other received acoustic signal, a transmission of the first received acoustic signal, or combinations thereof. Further, the comparison indicates at least one of time-of-flight of the acoustic signal and/or change in phase as a function of frequency. Further still, the apparatus may include the property to be an indication of at least one of: sound speed of the fluid; presence of gas bubbles in the fluid; or viscosity of the fluid. It is possible that the at least one acoustic transmitter includes an acoustic transducer, wherein the at least one acoustic receiver includes an array of acoustic transducers.

According to one aspect of the invention, the apparatus may further include the acoustic transducers being: ring-shaped; button-shaped; disk-shaped; or a combination thereof. It is possible that the acoustic transmitter and acoustic receiver may be in direct contact with the fluid. Wherein, the fluid includes borehole mud and/or formation fluid. Further, the tube can be part of a tool string. Further still, the apparatus may further include a mandrel disposed through the cavity of the tube, connecting portions of the tool string on opposite ends of the tube.

According to another embodiment of the invention, the invention can include a method for facilitating analysis of subterranean formations. The method includes causing a tube having a cavity to become filled with a downhole fluid. The method further includes generating, with at least one acoustic transmitter, at least one acoustic signal which can be propagated through the downhole fluid in the tube cavity. The method also includes receiving, with at least one acoustic receiver, the at least one acoustic signal, then comparing a characteristic of a first received acoustic signal of the at least one acoustic signal and a second signal. Finally, the method includes calculating a property of the fluid based on the comparison.

According to one aspect of the invention, the method may include the further step of selecting the second signal from the group consisting of at least one other received acoustic signal, a transmission of the first received acoustic signal, or combinations thereof. Further still, the method can include the comparing step to indicate at least one of time-of-flight of the acoustic signal and/or change in phase as a function of frequency. It is possible that the method includes the property of indicating at least one of sound speed of the fluid, presence of gas bubbles in the fluid, or viscosity of the fluid.

According to one aspect of the invention, the method may include the at least one acoustic transmitter having an acoustic transducer. The method may further include the at least one acoustic receiver having an array of acoustic transducers. Wherein the acoustic transducers can be one of: ring-shaped, button-shaped, disk-shaped, or a combination thereof. Further still, the method can include the acoustic transmitter and acoustic receiver that is in direct contact with the fluid, wherein the fluid includes borehole mud and/or formation fluid. Further, it is possible the tube can be part of a tool string. The method may further include a mandrel disposed through the cavity of the tube, connecting portions of the tool string on opposite ends of the tube.

According to another embodiment of the invention, the invention can include a device for facilitating analysis of formations. The device includes a tube filled with a fluid. The device further includes at least one acoustic transmitter operable to generate one or more acoustic signal which can be propagated through the fluid in a cavity of the tube. The device also includes at least one acoustic receiver operable to receive the one or more acoustic signal. Finally, the device includes means to operatively compare a characteristic of a first received acoustic signal of the one or more acoustic signal and a second signal, so as to calculate one or more property of the fluid based on the comparison.

Further features and advantages of the invention will become more readily apparent from the following detailed description when taken in conjunction with the accompanying Drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 4 is a side view of an integrated sensor tube in the tool string for measuring mud speed in a wireline configuration according to an aspect of the invention;

FIGS. 5 and 6 are cross sectional view of embodiments of the sensor tube of FIG. 4 taken along section a-a, according to an aspect of the invention;

FIGS. 7 through 9 illustrate and alternative embodiment adapted for measuring mud speed in logging-while-drilling according to an aspect of the invention.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

The present invention is directed to an apparatus for facilitating analysis of a subterranean formation. The apparatus can comprise of a tube having the inside filled with a downhole fluid. The apparatus further can include at least one acoustic transmitter operable to generate at least one acoustic signal which is propagated through the downhole fluid in the tube cavity. Further, the apparatus can include at least one acoustic receiver operable to receive the acoustic signal. The apparatus also includes circuitry operative to compare a characteristic of the at least one received acoustic signal with at least one other signal so as to calculate a property of the fluid based on the comparison. The at least one other signal can be either at least one other received acoustic signal, the generated acoustic signal, or both. The property of the fluid may be stored in a memory, sent to the surface via telemetry, or both.

Figure 1:
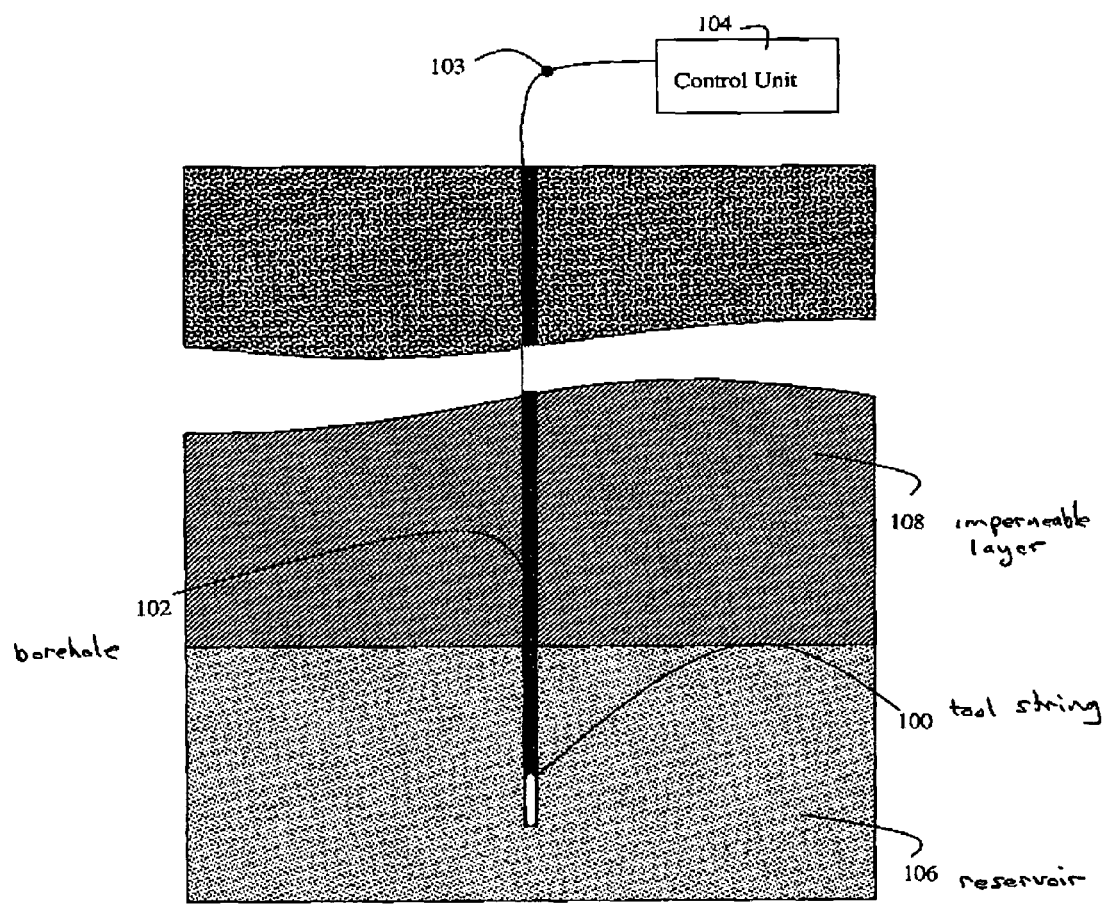
FIG. 1 illustrates a tool string in a borehole according to an aspect of the invention.

Referring to FIG. 1, a tool string (also referred as "tool") (100) is utilized to measure physical, chemical, and structural characteristics of formations surrounding a borehole (102). The tool string (100) may be part of a wireline logging tool string or logging-while-drilling tool string, and is operable in response to a control unit (104) which may be disposed at the surface. The control unit (104) can be equipped with processors and memory to facilitate data analysis, data storage, and generation of a reservoir model, among other things. Wireline cable or drill string connects the tool string (100) to the control unit (104). The tool string (100) is lowered into the borehole (102) to measure physical properties associated with the formation, which typically includes a reservoir (106) adjacent to an impermeable layer (108), and various other layers which make up the overburden. Data gathered by the tool string (100) may be communicated to the control unit in real time via the wireline cable. The data is then stored in control unit memory and utilized to generate the reservoir model.

In addition to various sensors known in the art, the tool string (100) is equipped with a sensor that utilizes tube waves to measure the speed of sound of a fluid (or the inverse metric, "sound slowness"). Acoustical pressure pulses can propagate in a fluid-filled tube with relatively little dispersion and attenuation at low frequencies where the wavelength is greater than the inner diameter of the tube. Low frequency tube wave speed CT can thus be represented as:

$$c_T = \left[\rho\left(\frac{1}{B} + \frac{1}{M}\right)\right]^{-1/2},$$

and $$M = \frac{E(a^2 - b^2)}{2[(1+V)(a^2+b^2) - 2Vb^2]},$$

where E (Young's modulus, $2 \times 10^{11}$ Pa for steel), v (Poisson's ratio, 0.3 for steel), a (outer radius), and b (inner radius) are parameters for the tube, and where $\rho$ (density), and B (bulk modulus) are parameters of the fluid. For a water-filled steel tube having an ID dimension of 5 mm, the low frequency range includes frequencies of about 100 kHz and below. For fluids of lower sound speed than water, such as most petroleum fluids, the range of low frequency is below 100 kHz. The parameter M in the equations above may be considered the equivalent modulus or rigidity of the tube. With known parameters of a given tube, and independently measured fluid density, the fluid speed c and compressibility $\beta$ can therefore be calculated as follows:

$$c = \left[c_T^{-2} - \frac{\rho}{M}\right]^{-1/2},$$

and $$\beta = \frac{1}{\rho c^2}.$$

These equations suggest that tube wave speed is lower than the sound speed in a free field of the fluid. The greater the thickness of the tube wall, the stiffer the tube, and the closer the tube wave speed to the fluid speed. In view of practical dimensional constraints of typical wellbores used in petroleum fluid recovery, the parameter M is one to two orders of magnitude greater than B for most petroleum fluids, thus indicating a small difference between the tube wave speed and the free field sound speed of the fluid. In some applications, before the fluid density is available or applied, the fluid speed can be estimated by:

$$c = \left[c_T^{-2} - \frac{\rho^*}{M}\right]^{-1/2},$$

where $\rho^*$ is an estimated or "nominal" fluid density. Assuming M is 10 times greater than B, an uncertainty of 10% in the estimated fluid density $\rho^*$ results in only about 0.5% uncertainty of sound speed c. Consequently, a practical tubewave-based sensor can be constructed for use in wellbores of dimensions such as those associated with petroleum fluid recovery (and also wellbores of other dimensions).

Figure 2:
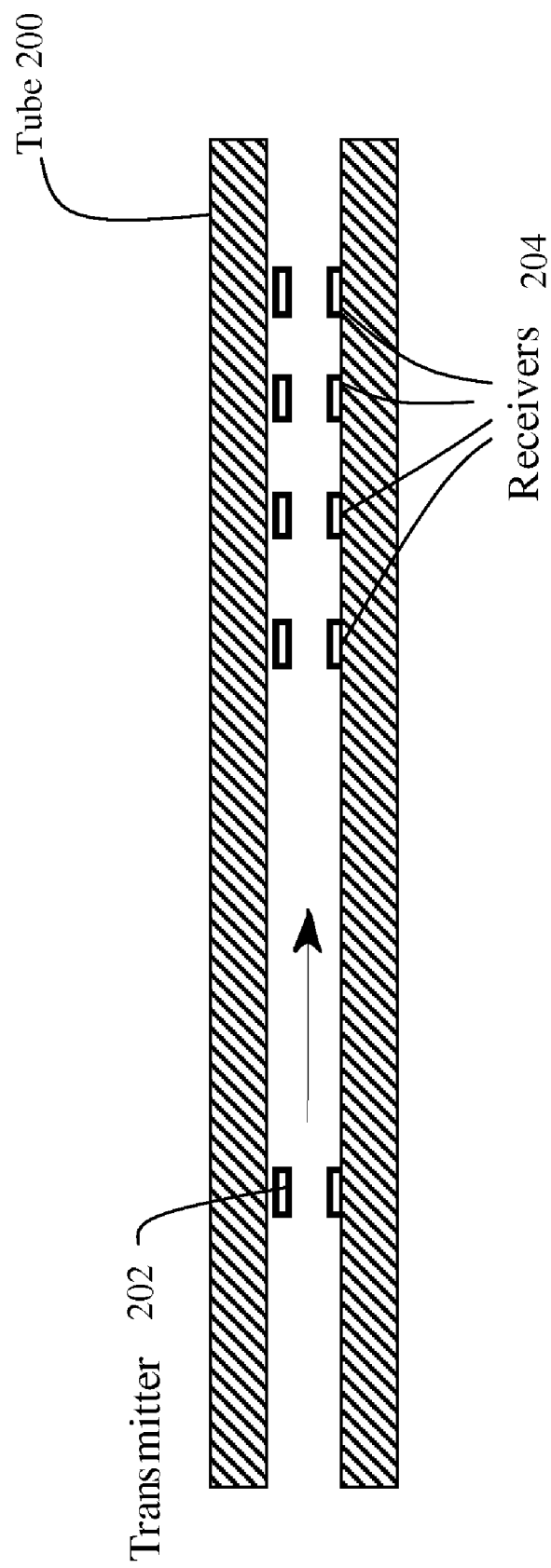
FIG. 2 illustrates an embodiment of a sensor tube for measuring sound speed of a fluid according to an aspect of the invention.

Referring to FIGS. 1 and 2, an embodiment of the tube-wave-based sensor can include a tube (200) with an acoustic source and an acoustic receiver. Either or both of the sensor and control unit (104) may include firing control circuitry, detection circuitry, and data processing hardware and software, among other things. The acoustic source includes at least one transmitter (202), and the acoustic receiver includes at least one receiver (204) (an array illustrated in FIG. 2). The acoustic source and acoustic receiver (204) may include, for example, transducers made of piezoceramic or some other material. The tube (200) may be made of steel or other materials. For example, the illustrated transmitter (202) and receivers (204) can be rings, which may be whole or split, and fitted inside the tube (200).

Figure 3:
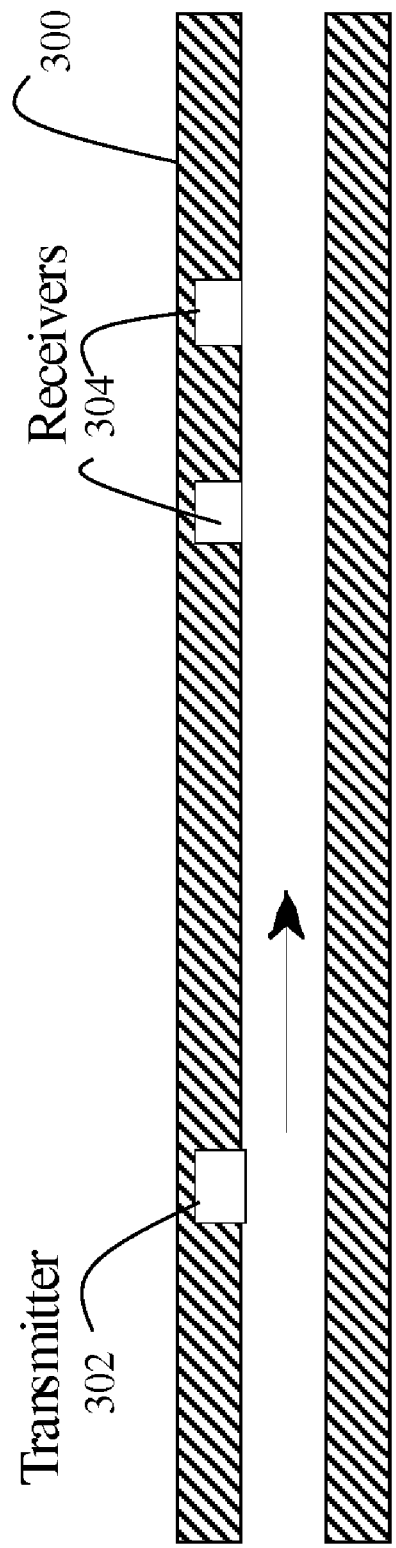
FIG. 3 illustrates an alternative embodiment of the sensor tube according to an aspect of the invention.

Referring to FIG. 3, in an alternative embodiment transmitter (302) and receivers (304) are buttons or disks that can be fitted inside "T-branches" of the tube (300).

According to embodiments of the invention as illustrated in both FIG. 2 and FIG. 3, the active elements of the sensor (transmitters and receivers) can be in direct contact with the fluid inside the tube in order to enhance tube wave signal strength and mitigate the energy distributed into other modes, such as extensional mode propagating along the tube. It is feasible, though acoustically less efficient, to couple the acoustic energy of tube waves through the tube wall with transducers mounted outside the tube. Further, although transducers are shown as the transmitters, it should be noted that various alternative techniques might be utilized to generate tube waves in the sensor. For example, a sudden change of the flow, such as turning on and off the flow, can generate tube waves. However, the frequency content and repetition rate of a flow-interruption source may be more difficult to control than a piezoelectric source.

According to aspects of the invention, in each of the illustrated embodiments there is a distance of about two wavelengths between the acoustic source and the nearest receiver of the receiver array to allow the tube waves to fully develop and to permit measurements to be made in far field. This spacing between the acoustic source and the first receiver can be modified based on requirements. Some design parameters relevant to frequency band can include tube ID, transmitter-receiver (TR) spacing, aperture of the receiver array, transducer frequency response, firing circuitry, and receiving circuitry, among other things. The excitation of tube waves is stronger for low frequencies. However, a non-resonant piezoceramic source has a 12 dB/octave output increase as a function of frequency. The spectrum of the measured tube wave is the combination (product) of these factors: excitation, transducer response, and the frequency response of the electronic driving as well as receiving circuits. The selection of measurement frequency range should include consideration of dimensional constraints and desired sampling volume. Subject to dimensional constraints, the tube may be positioned in various ways relative to the tool string to sample downhole fluids of interest. Further, the tube may be situated parallel to the axis of the tool string such that fluid freely flows through the tube, thereby continually refilling the tube with "local" fluid.

Alternative embodiments of the sensor tube suitable for wireline tools are illustrated in FIGS. 4 through 6. These embodiments include tubes (400, 500), for example are integral to the tool string (100). The integral tubes have input and output openings through the outer walls of the tools string, and borehole mud flows through these openings in response to tool motion, making these embodiments particularly suited to measuring borehole mud sound speed. The tool string has a cylindrical body with an internal cavity that function as the tubes (400, 500). A transmitter (402) and a receiver array (404) are disposed along inside walls of the tool string body. Tube ID, and hence cavity diameter, is selected based on the frequency range of interest. Tube waves are strongly excited and dominant at lower frequencies, while other monopole modes become more significant at higher frequencies. The transition between low and high frequency range in this context depends on the ID of the tube. In terms of operation, the greater the ID, the less the chance of the tube becoming clogged by borehole debris, and the more reliable the mud sampling. In terms tube material and thickness, the greater the tube rigidity, the flatter dispersion at low frequencies and less sensitive the tube mode is to fluid density.

The embodiment of FIG. 6 differs from that of FIG. 5 in that it includes a central mandrel (502) which connects segments of the tool string body on opposite sides of the tube (500). The mandrel (502) provides additional rigidity and strength. In the embodiment of FIG. 6 the tube waves are generated and propagate in the annulus between the mandrel and the tool body. The characteristics of the tube waves in the annulus are similar to that in a tube without a mandrel (e.g., FIG. 5). As in the previously described embodiments, transducers used as transmitters and receivers may be non-resonant piezoelectric devices. The spectrum of the measured tube wave is the combination (product) of excitation, the electronic drive, and the frequency response of the transducers and receiving circuits. The transducers should also be selected for mechanical ruggedness and avoidance of impeding the mud-flow. Ring transducers (either split or as sectors) embedded in inner grooves and T-transducers inserted through the wall of the tube might be used. T-R spacing and receiver aperture are each a significant fraction of one wavelength for enhanced measurement accuracy.

Referring to FIGS. 7 through 9, an alternative embodiment is adapted for logging-while-drilling (LWD). The LWD embodiment includes two ports (700) interconnected by a tube (802). A mud channel (804) may be routed away from the tube (802) if necessary. Borehole mud flows through the tube during drilling operations, thereby helping to ensure that measurements are made on local mud. Transducers (806) are disposed in the tube and operated in the manner already described above.

Figure 10:
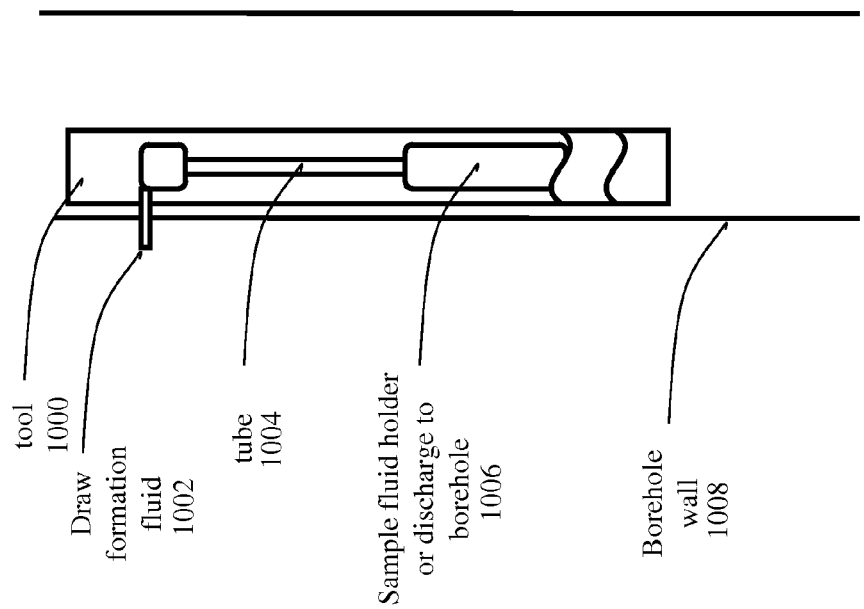
FIG. 10 illustrates an alternative embodiment adapted for measuring the sound speed of formation fluid with tube waves according to an aspect of the invention.

FIG. 10 illustrates an alternative embodiment adapted for measuring the sound speed of formation fluid with tube waves. In this embodiment a tool (1000) is equipped with a transverse draw tube (1002), a measurement tube (1004), and a sample holder chamber (1006). The draw tube (1002) is disposed transverse to the axis defined by the tool string (and the borehole), such that the tube (1002) can be pressed against and into the borehole wall (1008) to extract fluid from the formation for testing. The transverse tube may also be used to sample fluid in the borehole, i.e., borehole mud. In either case, the fluid to be tested flows into the measurement tube (1004), where it is subjected to test as already described above. The measurement tube (1004) may be evacuated following measurement so that a subsequent measurement will be made on a fresh sample. In particular, fluid may be discharged into the sample holder chamber (1006). Isolation valves may be employed to selectably isolate the draw tube, measurement tube and discharge chamber from one another. Alternatively, fluid may be discharged directly into the borehole rather than into a discharge chamber.

FIGS. 1-10 show an aspect of the invention, where fluid sound speed measurements can be taken in either the time domain or frequency domain. To take a measurement in the time domain, pressure pulses are generated at the acoustic source and received across the receiver array. Based on known firing time of transmitter and arrival times at receivers, time-of-flight is measured and recorded. The sound speed of the fluid in the tube can then be calculated from the time-of-flight data. According to one aspect of the invention, one method for measuring the time-of-flight can be first motion detection. With multiple receivers in the array, standard sonic processing techniques can be applied, such as "Slowness Time Coherence" described in Kimball, C. V. and Marzetta, T. L., Semblance Processing of Borehole Acoustic Array Data, Geophysics, Vol. 49, No. 3, March 1986, p. 274-281. Another standard processing technique that might be utilized is Prony's method, such as described in Lang, S. W., Kurkjian, A. L., McClellan, J. H., Morris, C. F., and Parks, T. W., Estimating Slowness Dispersion from Arrays of Sonic Logging Waveforms, Geophysics, Vol. 52, No. 4, April 1987 pp 530-544. Prony's method makes no assumptions about the speed dependence on frequency, and is thus useful for examining the speed dispersion as a function of frequency. However, Prony's method tends to be computationally more intensive than slowness time coherence. To take a measurement in the frequency domain the method described in Chang, S. K. and Hsu, C. J., Methods and Apparatus for Discrete Frequency Tube Wave Logging of Boreholes, U.S. Pat. No. 5,331,604, Jul. 19, 1994 may be utilized. In accordance to the above-mentioned technique, the phase is as a function of frequency, as opposed to the pressure pulse as a function of time, is measured at the receivers and used to calculate sound speed.

According to another aspect of the invention, the tube wave-based sensor can be utilized for other measurements related to the sound speed of fluids. For example, tube wave speed can be measured continuously during any pressure build-up or draw-down in order to detect the presence of gas. The presence of gas bubbles in a liquid increases the averaged bulk compressibility, and thus reduces the sound speed. Because the tube wave speed is closely related to the fluid speed, deviation of the tube wave speed from either the normal trend over the depth of the well or the expected range based on a priori knowledge of the mud can be an indicator of the presence of gas in the mud. The sensor can also be used for fluid viscosity measurement. The attenuation of tube waves is related to the dissipation at the tube wall and in the bulk of the mud. Thus, it is possible to estimate mud attenuation from tube wave data.

It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A borehole logging tool for facilitating analysis of fluids in subterranean formations, the tool comprising:
   a tube having a cavity configured to be filled with a fluid;
   at least one acoustic source disposed at a first axial position of the tube and operable to generate at least one acoustic signal comprising a tube wave, which is propagated in an axial direction through the fluid in the cavity of the tube;

at least one acoustic receiver disposed at a second axial position of the tube different from the first axial position and operable to receive a first received acoustic signal in response to the at least one acoustic signal generated by the at least one acoustic source;

circuitry operative to (1) compare a characteristic of the first received acoustic signal and a second signal to calculate tube wave data based on the comparison and (2) calculate a free field sound speed of the fluid based on the tube wave data.

2. The borehole logging tool of claim 1, wherein the second signal is selected from the group consisting of: (1) at least one other received acoustic signal, (2) a signal driving the at least one acoustic transmitter, or (3) some combination thereof.

3. The borehole logging tool of claim 1, wherein the tube wave data is at least one of: (1) time-of-flight data and (2) change in phase as a function of frequency data.

4. The borehole logging tool of claim 1, wherein the at least one acoustic source includes an acoustic transducer.

5. The borehole logging tool of claim 1, wherein the at least one acoustic receiver includes an array of acoustic transducers.

6. The borehole logging tool of claim 5, wherein the array of acoustic transducers are one of (1) ring-shaped, (2) button-shaped, (3) disk-shaped, or (4) some combination thereof.

7. The borehole logging tool of claim 1, wherein the at least one acoustic source and the at least one acoustic receiver are in direct contact with the fluid.

8. The borehole logging tool of claim 1, wherein the fluid includes one of (1) a borehole mud, (2) a formation fluid, or (3) some combination thereof.

9. The borehole logging tool of claim 8, wherein the fluid flows through the tube during logging operations.

10. The borehole logging tool of claim 1, wherein the tube is part of a tool string.

11. The borehole logging tool of claim 10, further including a mandrel disposed through the cavity of the tube, the mandrel connecting portions of the tool string on opposite ends of the tube.

12. A method for facilitating analysis of fluids in subterranean formations using a borehole logging tool, the method comprising:
    causing a tube having a tube cavity to become filled with a downhole fluid, wherein the borehole logging tool includes the tube;
    generating, with at least one acoustic source disposed at a first axial position of the tube, at least one acoustic signal comprising a tube wave, which is propagated in an axial direction through the downhole fluid in the tube cavity;
    receiving, with at least one acoustic receiver disposed at a second axial position of the tube different from the first axial position, a first received acoustic signal in response to the at least one acoustic signal generated by the at least one acoustic source;
    comparing a characteristic of the first received acoustic signal and a second signal to calculate tube wave data based on the comparison; and
    calculating a free field sound speed of the fluid based on the tube wave data.

13. The method of claim 12, wherein the second signal is selected from the group consisting of: (1) at least one other received acoustic signal, (2) a signal driving the at least one acoustic transmitter, or (3) some combination thereof.

14. The method of claim 12, wherein the comparison indicates at least one of: (1) a time-of-flight of the acoustic signal, (2) a change in phase as a function of frequency, or (3) some combination thereof.

15. The method of claim 12, wherein the at least one acoustic receiver includes an array of acoustic transducers.

16. The method of claim 15, wherein the array of acoustic transducers are one of (1) ring-shaped, (2) button-shaped, (3) disk-shaped, or (4) some combination thereof.

17. The method of claim 12, wherein the at least one acoustic source and at least one acoustic receiver are in direct contact with the fluid.

18. The method of claim 12, wherein the downhole fluid includes one of (1) a borehole mud, (2) a formation fluid, or (3) some combination thereof.

19. The method of claim 12, wherein the tube is part of a tool string.

20. The method of claim 19, further comprising: connecting portions of the tool string on opposite ends of the tube with a mandrel disposed through the cavity of the tube.

21. A logging-while-drilling device for facilitating analysis of fluid within formations, the device comprising:
    a mud channel;
    a tube having a tube cavity configured to be filled with a fluid, the tube being separate from the mud channel;
    at least one port interconnected with the tube, the at least one port configured to draw fluid into the tube;
    at least one acoustic source disposed at a first axial position of the tube and operable to generate one or more acoustic signal comprising a tube wave, which is propagated in an axial direction through the fluid in the tube cavity;
    at least one acoustic receiver disposed at a second axial position of the tube different from the first axial position and operable to receive a first received acoustic signal in response to the at least one acoustic signal generated by the at least one acoustic source; and
    circuitry operative to compare a characteristic of the first received acoustic signal and a second signal, so as to calculate at least one property of the fluid based on the comparison.

22. The borehole logging tool of claim 1, wherein the tube is part of a flow line.

23. The borehole logging tool of claim 1, wherein the tube is made of a material from the group consisting of: (1) a steel or (2) a material having a Young's modulus of approximately $2 \times 10^{11}$ Pa.

24. The borehole logging tool of claim 1, wherein the at least one acoustic signal is propagated at a frequency having a range approximately equal to or less than about 100 kHz.

25. The borehole logging tool of claim 1, wherein at least one of (1) the at least one acoustic source, (2) the at least one acoustic receiver, or (3) both are at least one of (1) attached to an inner surface of the tube, (2) integral with the tube so as to extend through an inner surface of the tube where the fluid flows, (3) integral with the tube position between an outer surface and the inner surface of the tube, (4) some combination thereof.

26. The borehole lodging tool of claim 1, wherein the tube wave data includes a tube wave speed, and the tube wave speed is used to calculate the free field sound speed of the fluid.

27. The method of claim 12, wherein the at least one acoustic signal is propagated through the downhole fluid in the cavity in a fluid flow direction.

28. The method of claim 12, wherein the tube wave consists of an interaction between an inner surface of the tube and the downhole fluid.

29. The method of claim 12, wherein the tube wave data includes a tube wave speed and the tube wave speed is used to calculate the free field sound speed of the fluid.

30. The device of claim 21, wherein the at least one property of the fluid is selected from the group consisting of: (1) sound speed of the fluid, (2) presence of gas bubbles in the fluid, or (3) a viscosity of the fluid.

31. The device of claim 21, wherein the circuitry (1) compares the characteristic of the first received acoustic signal and the second signal to calculate tube wave data and (2) calculates a free field sound speed of the fluid based on the tube wave data.

32. The device of claim 31, wherein the second signal is selected from the group consisting of: (1) at least one other received acoustic signal, (2) a signal driving the at least one acoustic transmitter, or (3) some combination thereof.

33. The device of claim 31, wherein the tube wave data is at least one of: (1) time-of-flight data and (2) change in phase as a function of frequency data.

34. The borehole logging tool of claim 1, wherein the borehole logging tool is a wireline tool.

35. The borehole logging tool of claim 1, wherein the borehole logging tool is a logging-while-drilling (LWD) tool.

\* \* \* \* \*